United States Patent [19]

Binder et al.

[11] Patent Number: 5,298,519
[45] Date of Patent: Mar. 29, 1994

[54] ACYLALS OF IMIDAZOLE-5-CARBOXYLIC ACID DERIVATIVES, AND THEIR USE AS ANGIOTENSIN (II) INHIBITORS

[75] Inventors: Dieter Binder, Wien; Josef Weinberger, Bad Hall, both of Austria

[73] Assignee: Chemish Pharmazeutische Forschungsgesellschaft m.b.H., Linz, Austria

[21] Appl. No.: 950,181

[22] Filed: Sep. 24, 1992

[30] Foreign Application Priority Data

Oct. 4, 1991 [AT] Austria ................... A 1987

[51] Int. Cl.⁵ ............... A61K 31/41; A61K 31/415; C07D 403/10
[52] U.S. Cl. ..................... 514/381; 548/253
[58] Field of Search ................ 548/253; 514/381

[56] References Cited

FOREIGN PATENT DOCUMENTS 0253310 1/1988 European Pat. Off. .
0401030 12/1990 European Pat. Off. .
0411507 2/1991 European Pat. Off. .
00281 1/1991 PCT Int'l Appl. .

Primary Examiner—Patricia L. Morris
Attorney, Agent, or Firm—Wenderoth, Lind & Ponack

[57] ABSTRACT

Novel imidazole-5-carboxylic acid acylals of the general formula

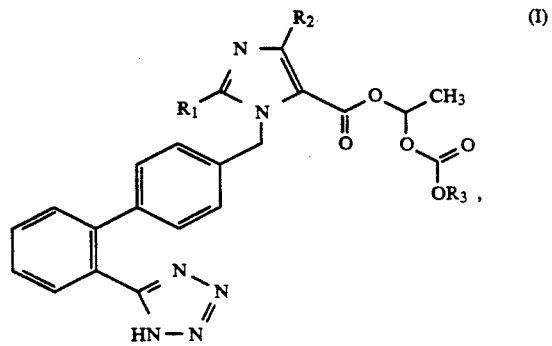

in which $R_1$ denotes an optionally unsaturated, straight-chain alkyl group having 1-6 carbon atoms, $R_2$ denotes hydrogen, chlorine, bromine, iodine or $CF_3$ and $R_3$ denotes $C_1$-$C_{10}$-alkyl, $C_3$-$C_7$-cycloalkyl or benzyl, and their pharmaceutically tolerable salts.

8 Claims, 9 Drawing Sheets

ACYLALS OF IMIDAZOLE-5-CARBOXYLIC ACID DERIVATIVES, AND THEIR USE AS ANGIOTENSIN (II) INHIBITORS

The invention relates to novel therapeutically useful acylals of imidazole-5-carboxylic acid derivatives and their salts, a process for their preparation and their use in medicaments having a hypotensive action.

A large number of compounds are already known which can be used for the treatment of high blood pressure caused by angiotensin II.

A known angiotensin II receptor antagonist, DuP 753 (2-n-butyl-4-chloro-5-hydroxymethyl-1-((2'-(1H-tetrazol-5-yl)biphenyl-4-yl)methyl)imidazole) is described, for example, in Journal of Pharmacology and Experimental Therapeutics, P. C. Wong et al., 1990, Vol. 225, pp. 211–217. However, DuP 753 is converted on in vivo administration to a non-competitive metabolite EXP 3174, (2-n-butyl-4-chloro-1-((2'-(1H-tetrazol-5-yl)biphenyl-4-yl)methyl)imidazole-5-carboxylic acid), which is responsible to a large extent for the duration of action of DuP 753. The disadvantage of non-competitive antagonists, however, is that they are irreversibly bound to the receptor and there cause changes in the cellular structure.

EP-A1-0253310 discloses, inter alia, angiotensin II receptor-blocking imidazolecarboxylic acids of the formula

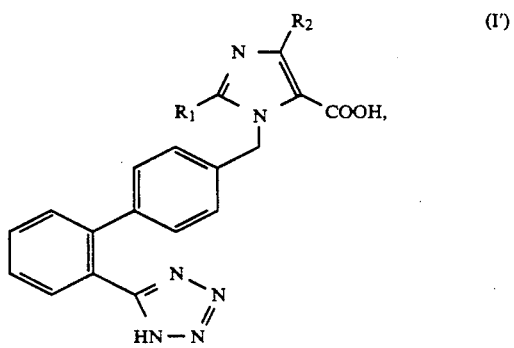

in which $R_1$ can denote an optionally unsaturated, straight-chain alkyl group having 1–6 carbon atoms and $R_2$ can denote hydrogen, chlorine, bromine, iodine and $CF_3$, which are distinguished by particularly potent action. On intravenous administration, these compounds show excellent hypotensive action. Their disadvantage is that, on oral administration, they are only absorbed to a small extent and achieve a lower potency of action or must be administered in higher doses.

The object of the present invention was thus to find purely competitive antagonists which, on oral administration, have an absorption which is several times better, and thus a higher activity, than the carboxylic acids of the general formula (I') and on passage through the intestine into the blood are again present as free carboxylic acids. It has now unexpectedly been possible to achieve this object with the acylals and esters according to the invention.

The present invention thus relates to novel compounds of the general formula

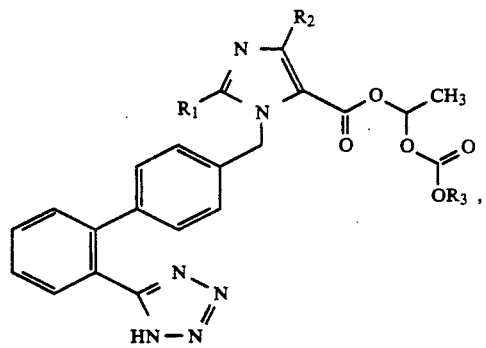

in which $R_1$ denotes an optionally unsaturated, straight-chain alkyl group having 1–6 carbon atoms, $R_2$ denotes hydrogen, chlorine, bromine, iodine or $CF_3$ and $R_3$ denotes $C_1$–$C_{10}$-alkyl, $C_3$–$C_7$-cycloalkyl or benzyl, and their pharmaceutically tolerable salts.

A preferred class of compounds are those in which $R_1$ denotes butyl, $R_2$ denotes chlorine and $R_3$ denotes ethyl.

Figure 1A:
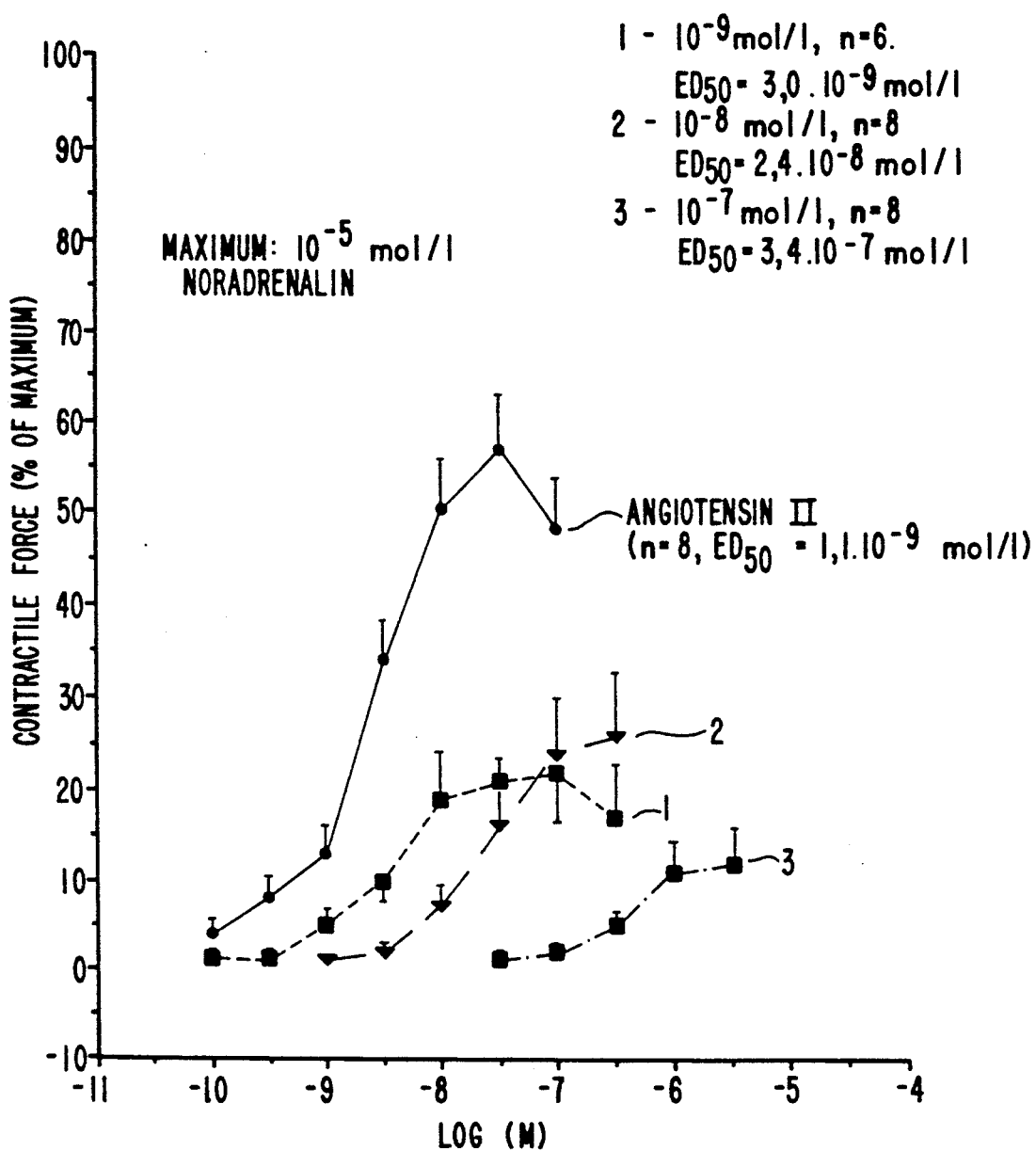
FIGS. 1a) and b) depict the action of a compound according to the present invention and a compound of the prior art on the contractile force of an isolated rat aorta.

A further subject of the present invention is a process for the preparation of the novel compounds of the formula (I) in which $R_1$, $R_2$ and $R_3$ have the above meaning, which consists in reacting, in step a), a compound of the formula

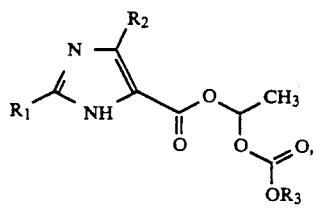

in which $R_1$, $R_2$ and $R_3$ have the above meaning, with a compound of the formula

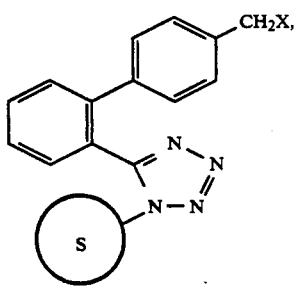

in which X denotes chlorine, bromine or iodine and —Ⓢ denotes the triphenylmethyl protective group, heating the compound thus obtained of the formula

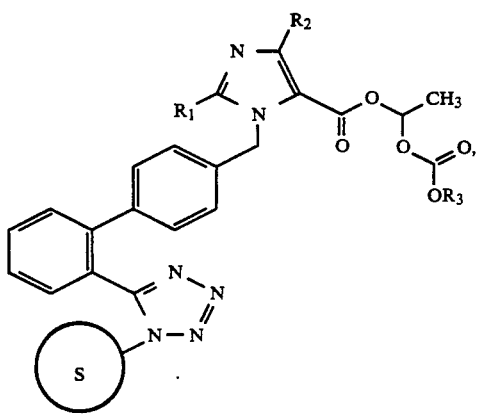

in which $R_1$, $R_2$, $R_3$ and —Ⓢ have the above meaning, with a lower aliphatic alcohol in step b) and optionally converting the compound of the formula (I) that is obtained, which because of its amorphous character, customarily does not crystallise, into a pharmaceutically tolerable, crystalline salt using inorganic or organic bases.

The reaction according to the invention is best carried out in step a) by heating a solution of the compounds of the general formulae II and III in an anhydrous, organic solvent which is inert to the reaction, such as, for example, ether, dioxane, THF, acetone, dimethylformamide or dimethyl sulphoxide, in the presence of one equivalent of solid potassium carbonate. The most favourable reaction temperature is in this case between 20° and 100° C. and the reaction time, in dependence on this, is 0.5 to 20 seconds.

The following removal, in step b), of the triphenylmethyl protective group —Ⓢ from the compounds of the general formula IV obtained is carried out by boiling in a lower aliphatic alcohol, such as, for example, methanol or ethanol, and the reaction time is in this case between 5 minutes and 10 hours. The compounds of the general formula (I) obtained during the reaction in process step b) can be converted into their pharmaceutically utilisable salts in a customary manner using inorganic and organic bases. Salt formation can be carried out, for example, by dissolving the said compounds of the formula (I) in a suitable solvent, for example water, a lower aliphatic alcohol, THF, dioxane, benzene, $CH_2Cl_2$, $CHCl_3$, diethyl ether, DMF or DMSO, adding an equivalent amount of the desired base, providing for thorough mixing and, after salt formation is complete, stripping off the solvent in vacuo. The salts can optionally be recrystallised after isolation.

Pharmaceutically utilisable salts are, for example, metal salts, in particular alkali metal or alkaline earth metal salts, such as the sodium, potassium, magnesium or calcium salts. Other pharmaceutical salts are, for example, easily crystallising ammonium salts. The latter are derived from ammonia or organic amines, for example mono-, di- or tri-lower(alkyl, cycloalkyl or hydroxyalkyl)amines, lower alkylenediamines or (hydroxylower alkyl or aryl-lower alkyl)ammonium bases, for example methylamine, diethylamine, triethylamine, dicyclohexylamine, triethanolamine, ethylenediamine, tris(hydroxymethyl)- aminomethane, benzyltrimethylammonium hydroxide and the like.

The compounds of the general formula (II) can be prepared starting from compounds of the formula (V) in which $R_1$ and $R_2$ have the above meaning, according to the following reaction scheme by chemical working methods which are customary and familiar to the person skilled in the art.

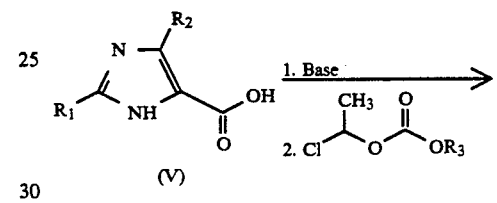

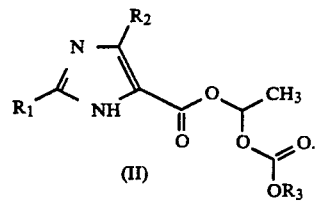

The compounds of the general formulae (III) and (V) are known from the literature (D. J. Carini et al., EP 0 324 377, 1989).

The novel compounds of the general formula I and their salts are orally active and suppress the vasoconstrictive and hypertensive action of angiotensin II and exhibit excellent hypotensive action in animal models.

As a result of these pharmacological properties, the novel compounds can be used on their own or mixed with other active substances in the form of a customary pharmaceutical preparation as medicaments for the treatment of high blood pressure and other cardiovascular disorders.

The invention therefore furthermore relates to medicaments which contain the compounds of the general formula (I) according to the invention or their salts, as the hypotensive active substance, on their own or mixed with other active substances in the form of a customary oral pharmaceutical composition. The compounds according to the invention can be orally administered in the form of tablets or capsules which contain a unit dose of the compound together with diluents, such as maize starch, calcium carbonate, dicalcium phosphate, alginic acid, lactose, magnesium stearate, Primogel or talc. The tablets are prepared in a conventional manner by granulating the ingredients and pressing, and the capsules by filling into hard gelatine capsules of suitable size.

For oral administration in humans, the daily dose value of a compound according to the invention is expected to be in the range from 0.1 to 30 mg/kg per day for a typical adult patient of weight 70 kg. Tablets or capsules can therefore customarily contain 0.1 to 50 mg of active compound for oral administration up to three times during the day.

Of course, however, the physician will determine in each case the actual dose which is most suitable for the individual patient, it being possible for this to vary with the age, the weight and the response of the patient.

EXAMPLE 1

1-Ethoxycarbonyloxyethyl 2-butyl-4-chloro-1-((2'-(1H-tetrazol-5-yl)biphenyl-4-yl)methyl-1H-imidazole-5-carboxylate 8.0 g (10.06 mmol) of 1-ethoxycarbonyloxyethyl-2-butyl-4-chloro-1-((2'-N-triphenyl-1H-tetrazol)-5-yl)biphenyl-4-yl)methyl)-1H-imidazolecarboxylate are heated to boiling for 3 hours in 175 ml of methanol, the solvent is stripped off and the crude product obtained is subjected to a column chromatographic separation ($Et_2O$; 400 g of silica gel 60).

Yield: 5.0 g of colourless amorphous substance

| Microelemental analysis: $C_{27}H_{29}ClN_6O_5$ | | MW: 553.02 | |
|---|---|---|---|
| | C | H | N |
| calculated | 58.64 | 5.29 | 15.29 |
| found | 58.3 | 5.4 | 15.3 |

$^1$H-NMR: ($CDCl_3$)

δ(ppm): 7.91 (dd, 1H, Biph-H3'); 7.64–7.43 (m, 2H Biph-H4', H5'); 7.41 (dd, 1H, Biph-H6'); 7.10 (AA'; 2H, Biph-H3, H5); 6.89 (BB', 2H, Biph-H2, H6); 6.82 (q, 1H, C$\underline{H}$—$CH_3$); 5.48 (s, 2H, Biph—$CH_2$); 4.15 (q, 2H, —C$\underline{H}$$_2$—$CH_3$); 2.66 (t, 2H, Bul—$CH_2$—); 1.63 (m, 2H, Bu-2—$CH_2$—)'; 1.54 (d, 3H, CH—C$\underline{H}$$_3$); 1.32 (m, 2H, Bu-3—$CH_2$—); 1.21 (t, 3H, —$CH_2$—C$\underline{H}$$_3$); 0.86 (t, 3H, bu4—$CH_3$)

$^{13}$C-NMR: ($CDCl_3$)

δ(ppm): 156.71; 156.59; 153.20; 152.37; 140.63; 139.21; 136.54; 135.23; 130.51; 130.37; 129.94; 129.18; 127.45; 125.94; 125.72; 115.74; 91.37; 64.16; 47.80; 28.58; 25.83; 21.53; 19.22; 13.85; 13.50

EXAMPLE 2

1-Ethoxycarbonyloxyethyl 2-butyl-4-chloro-1-((2'-(1H-tetrazol-5-yl)biphenyl-4-yl)methyl)-1H-imidazole-5-carboxylate, sodium salt 0.41 g (3.62 mmol) of sodium trimethylsilanolate in 3 ml of dichloromethane is added dropwise to 2.0 g (3.62 mmol) of 1-ethoxycarbonyloxyethyl 2-butyl-4-chloro-1-((2'-(1H-tetrazol-5-yl)biphenyl-4-yl)methyl)-1H-imidazole-5-carboxylate in 40 ml of dichloromethane, the mixture is stirred for 1 hour, the solvent is stripped off and the residue is crystallised in diisopropyl ether, filtered and digested 3× with cold diisopropyl ether.

Yield: 1.3 g of colourless crystals

M.p.: dec. from 138° C.

| Microelemental analysis: $C_{27}H_{28}ClN_6O_5Na\cdot H_2O$ | | MW: 593.02 | |
|---|---|---|---|
| | C | H | N |
| calculated | 54.69 | 5.10 | 14.17 |
| found | 54.47 | 5.08 | 14.28 |

$^1$H-NMR (DMSO) δ(ppm): 7.56 (dd, 1H, Biph-H3'); 7.41–7.23 (m, 3H, Biph-H4', H5', H6'); 7.10 (AA', 2H, Biph-H3, H5); 6.86 (BB', 2H, Biph-H2, H6); 6.78 (q, 1H, C$\underline{H}$—$CH_3$); 5.52 (AB, 2H, Biph—$CH_2$); 4.13 (q, 2H, —C$\underline{H}$$_2$—$CH_3$); 2.65 (t, 2H, Bul—$CH_2$—); 1.56 (m, 2H, Bu2—$CH_2$—); 1.48 (d, 3H, CH—C$\underline{H}$$_3$); 1.29 (m, 2H, Bu3—$CH_2$—); 1.19 (t, 3H, —$CH_2$—C$\underline{H}$$_3$); 0.82 (t, 3H, Bu4—$CH_3$) $^{13}$C-NMR (DMSO) δ(ppm): 160.66; 156.72; 153.19; 152.36; 141.20; 139.74; 136.52; 134.10; 132.54; 130.46; 130.00; 129.40; 127.21; 126.67; 125.14; 115.68; 91.38; 64.16; 47.84; 28.62; 25.87; 21.56; 19.27; 13.88; 13.58

The starting material can be prepared as follows:

1-Ethoxycarbonyloxyethyl 2-butyl-4-chloro-1H-imidazole-5-carboxylate 4.88 g (43.47 mmol) of sodium silanolate in 20 ml of THF are added dropwise to 7.66 g (37.80 mmol) of 2-butyl-4-chloro-1H-imidazole-5-carboxylic acid in 155 ml of hexamethylphosporamide and the mixture is stirred for 30 minutes.

6.34 g (41.58 mmol) of chloroethyl ethyl carbonate in 25 ml of hexamethylphosphoramide are added dropwise to this solution and the reaction mixture is kept for 1 hour at 80° C. It is poured into 760 ml of water, extracted with 8×75 ml of diethyl ether, and the combined organic phases are washed with 3×65 ml of aqueous sodium hydrogenate carbonate solution and with 3×100 ml of water. The organic phase is dried over sodium sulphate/active carbon and filtered, and the solvent is stripped off. The crude product obtained is subjected to a column chromatographic separation (EA:$CH_2Cl_2$=1:25; 300 g of silica gel 60).

Yield: 7.4 g of colourless crystals

M.P.: 108°–110° C.

| Microelemental analysis: $C_{13}H_{19}ClN_2O_5$ | | MW: 318.76 | |
|---|---|---|---|
| | C | H | N |
| calculated | 48.99 | 6.01 | 8.79 |
| found | 48.84 | 5.86 | 8.65 |

$^1$H-NMR ($CDCl_3$) δ(ppm): 6.92 (q, 1H, C$\underline{H}$—$CH_3$); 4.18 (q, 2H, —C$\underline{H}$$_2$—$CH_3$); 2.71 (t, 2H, Bul—$CH_2$—); 1.69 (m, 2H, Bu2—$CH_2$—); 1.57 (d, 3H, CH—C$\underline{H}$$_3$); 1.43 (m, 2H, Bu3—$CH_2$—); 12.8 (t, 3H, —$CH_2$—C$\underline{H}$$_3$); 0.86 (t, 3H, Bu4—$CH_3$)

$^{13}$C-NMR ($CDCl_3$) δ(ppm): 157.48; 152.95; 141.91; 136.71; 115.73; 91.47; 64.57; 29.90; 28.28; 22.13; 19.56; 14.00; 13.53

1-Ethoxycarbonyloxyethyl 2-butyl-4-chloro-1-((2'-(N-triphenyl-1H-tetrazol-5-yl)biphenyl-4-yl)methyl)-1H-imidazolecarboxylate 7.1 g (22.27 mmol) of 1-ethoxycarbonyloxyethyl 2-butyl-4-chloro-1H-imidazole-5-carboxylate, 15.52 g (27.84 mmol) of N-triphenylmethyl-5-(4'-bromomethyl-biphenyl-2-yl)-1H-tetrazole and 3.85 g (27.84 mmol) of potassium carbonate are stirred at 70° C. for 1.5 hours in 230 ml of DMF. After stripping off the solvent, the residue is partitioned between 250 ml of half-concentrated ammonium chloride solution and 100 ml of diethyl ether, the phases are separated and the aqueous phase is extracted with 4×50 ml of diethyl ether. The combined organic phases are washed with 5×50 ml of water, dried over sodium sulphate/active carbon and filtered, and the solvent is stripped off. The crude product obtained is subjected to a column chromatographic separation (Bz:Et$_2$O=6:1; 400 g of silica gel 60).
Yield: 9.65 g of colourless crystals
M.P.: 150°-153° C.

| Microelemental analysis: C$_{46}$H$_{43}$ClN$_6$O$_5$ | | MW: 795.34 | |
|---|---|---|---|
| | C | H | N |
| calculated | 69.47 | 5.45 | 10.57 |
| found | 69.39 | 5.65 | 10.74 |

$^1$H-NMR: (DMSO)
δ(ppm): 7.92 (dd, 1H, Biph-H3'); 7.54–7.39 (m, 2H, Biph-H5', H6'); 7.39–7.23 (m, 9H, Trit-H2, H4, H6); 7.21 (t, 1H, Biph-H4'); 7.10 (AA', 2H, Biph-H3, H5); 6.98–6.90 (m, 6H, Trit-H3, H5); 6.88 (q, 1H, $\overline{\text{CH}}$—CH$_3$); 6.81 (BB', 2H, Biph-H2, H6); 5.45 (A$\overline{\text{B}}$, 2H, Biph—CH$_2$); 4.19 (q, 2H, —$\overline{\text{CH}_2}$—CH$_3$); 2.50 (t, 2H, Bu-1—CH$_2$—); 1.64 (m 2H, $\overline{\text{Bu2}}$—CH$_2$—); 1.53 (d, 3H, CH—CH$_3$); 1.28 (m, 2H, Bu3—CH$_2$—); 1.27 (t, 3H, —$\overline{\text{CH}_2}$—CH$_3$); 0.86 (t, 3H, Bu4)—CH$_3$)

$^{13}$C-NMR: (DMSO) δ(ppm): 163.84; 147.40; 153.03; 152.92; 141.29; 141.13; 140.13; 140.64; 138.05; 134.39; 130.67; 130.19; 130.09; 129.87; 129.66; 128.17; 127.73; 127.54; 126.13; 125.53; 116.12; 91.28; 82.78; 64.34; 48.20; 29.15; 26.72; 22.17; 19.47; 14.02; 13.60

EXAMPLE 3

The affinity of the substances for the angiotensin II-1 subtype receptor was determined on adrenal cortex microsomes of rats (system: $^3$H-DuP 753). With an IC$_{50}$ of 79.4 nmol/l, the compound according to Example 1 showed lower affinity than DuP 753 (7.24 nmol/l) and EXP 3174 (7.87 nmol/l).

Figure 1B:
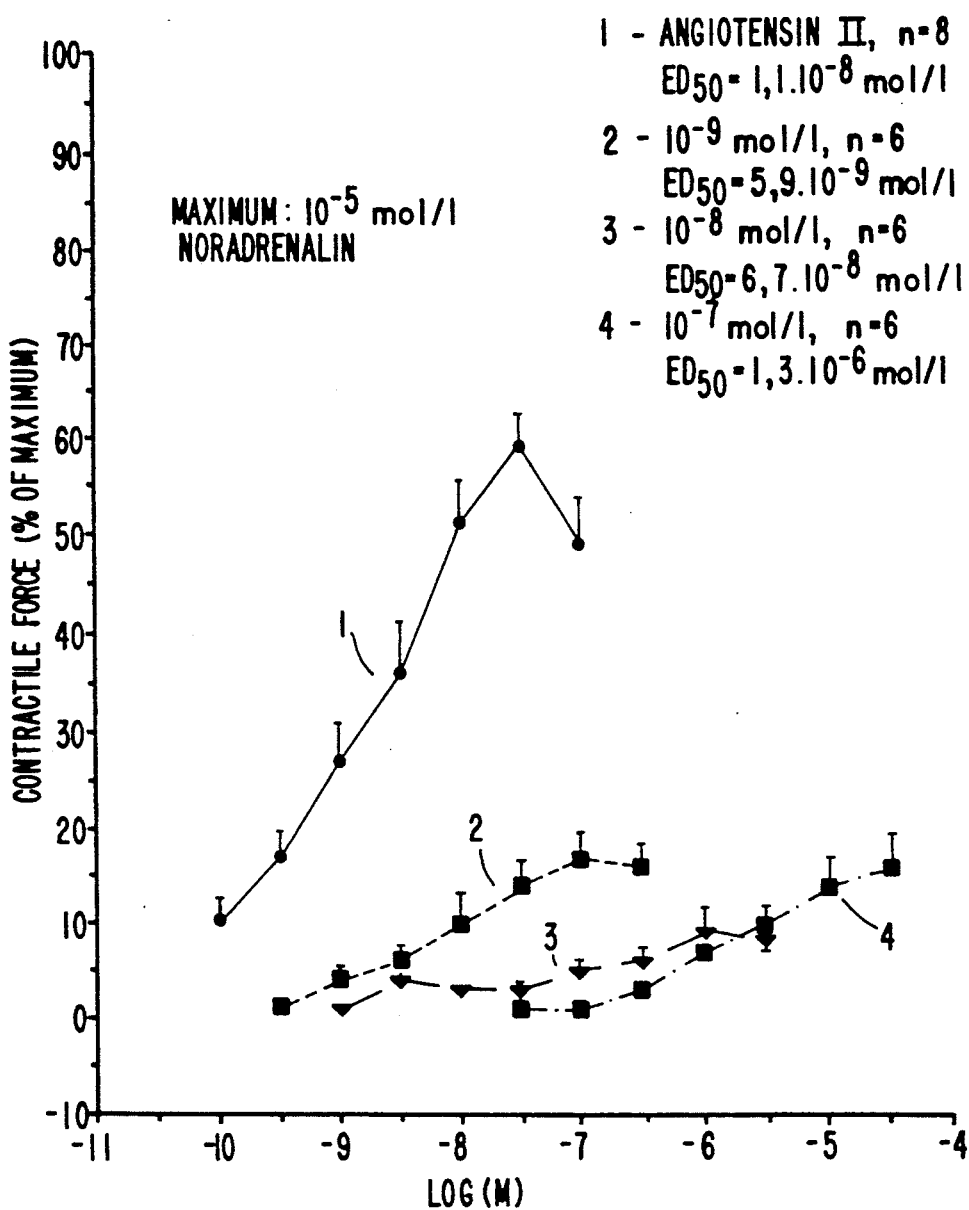

Investigations on isolated rat aorta have shown that the compound according to Example 1 and EXP 3174 are selective, non-competitive angiotensin II receptor antagonists. (FIG. 1)

Both substances reduced the maximum contraction due to angiotensin II in a dose-dependent manner ($10^9$–$10^{-7}$ mol/l), EXP 3174 acting in a comparatively more potent manner:

| Isolated rat aorta: % inhibition of the maximum contraction due to angiotensin II (3 × $10^{-7}$ mol/l): | | |
|---|---|---|
| mol/l | Compound according to Example 1 | EXP 3174 |
| $10^{-9}$ | 63 | 76 |
| $10^{-8}$ | 72 | 95 |
| $10^{-7}$ | 98 | 100 |

Figure 2A:
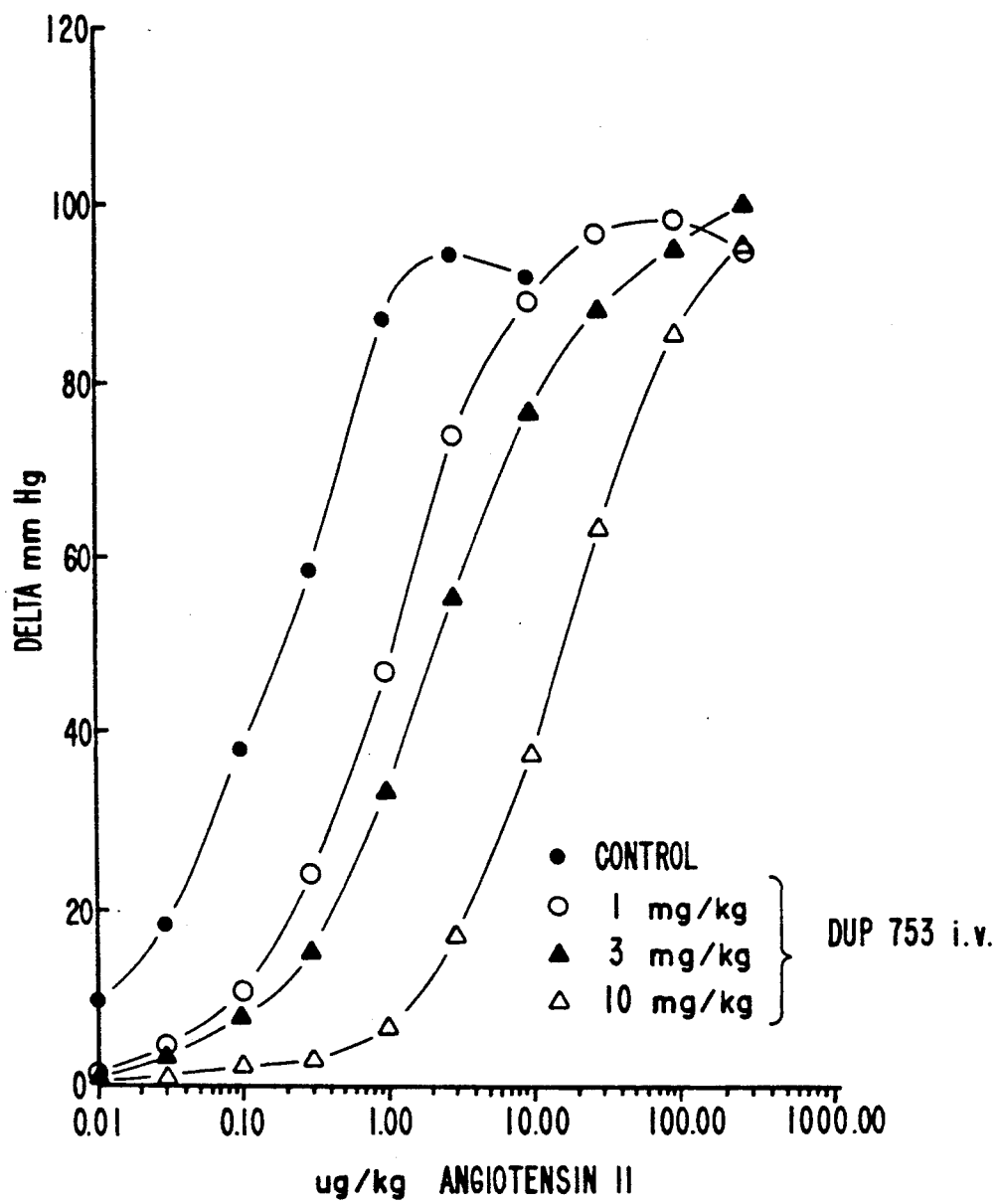
FIGS. 2a), b) and c) depict the effect of the presently claimed and known intravenously administered compounds on angiotensin II induced increases on diastolic blood pressure in pithed rats.
Figure 2B:
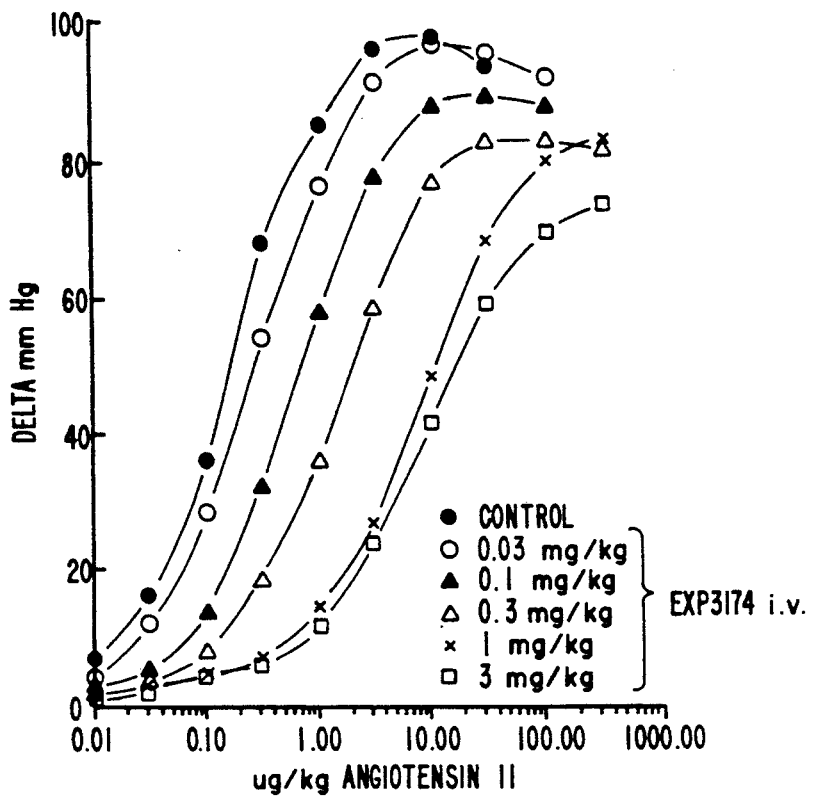
Figure 2C:
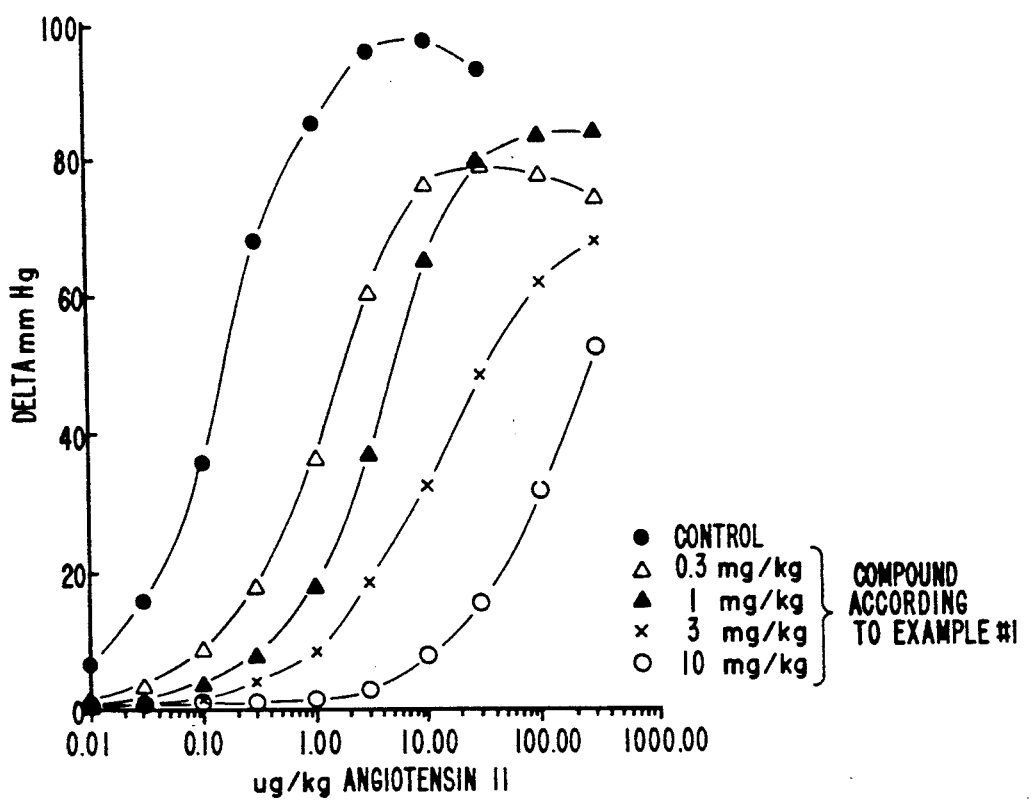
Figure 3A:
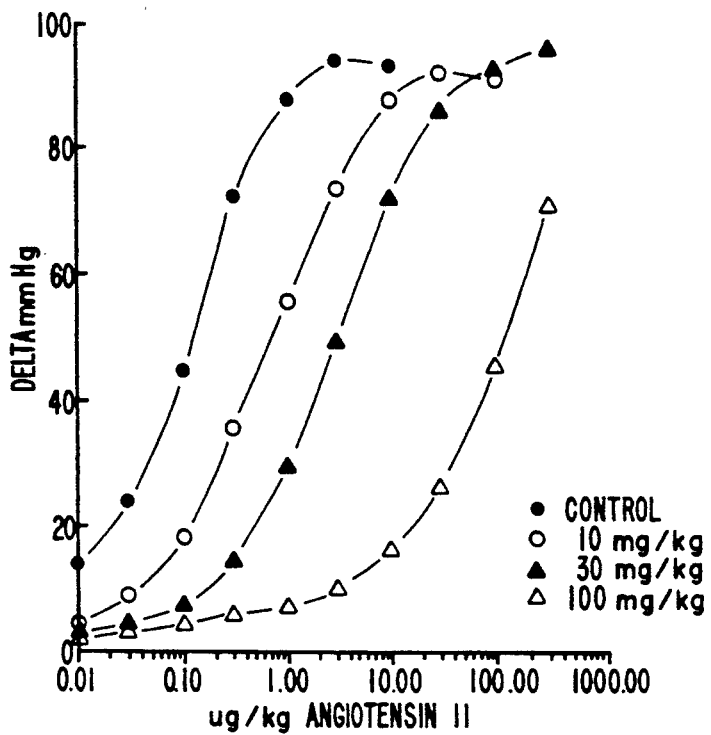
FIGS. 3a), b) and c) depict the effect of known and claimed intraduodenally administered compounds on angiotensin II induced increases of diastolic blood pressure in pithed rats.
Figure 3B:
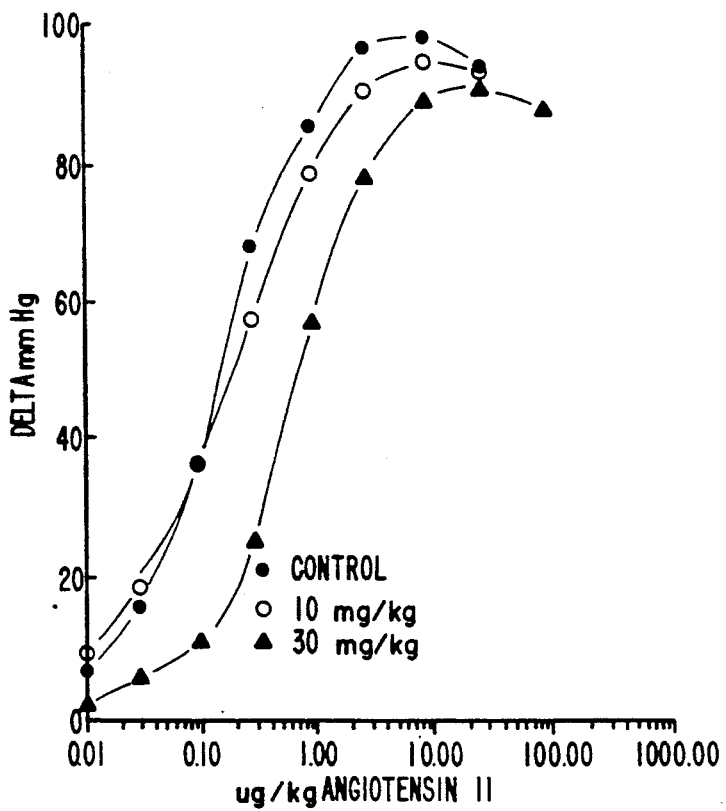
Figure 3C:
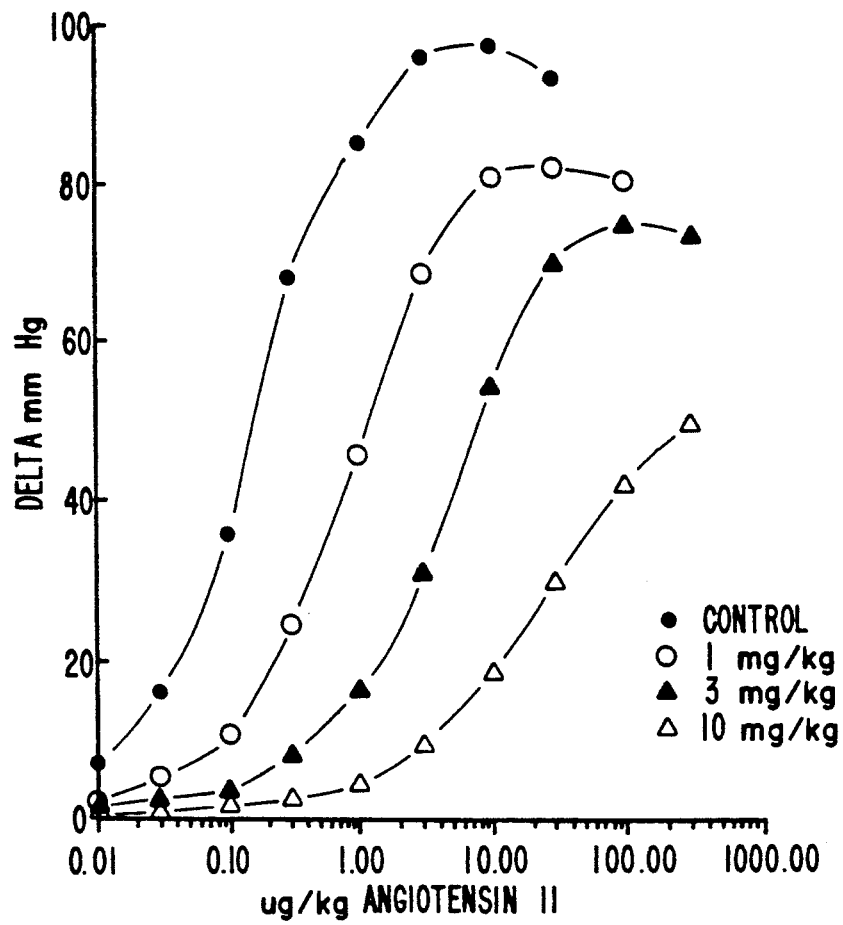

In pithed rats as well, the compound according to Example 1 and EXP 3174 inhibited the hypertensive action of agniotensin II in a non-competitive manner. In contrast to this, DuP 753 lead to a competitive inhibition, that is to say to a parallel shift to the right of the dose-response curve of angiotensin II without a reduction in the maximum effect (FIGS. 2, 3).

Figure 4:
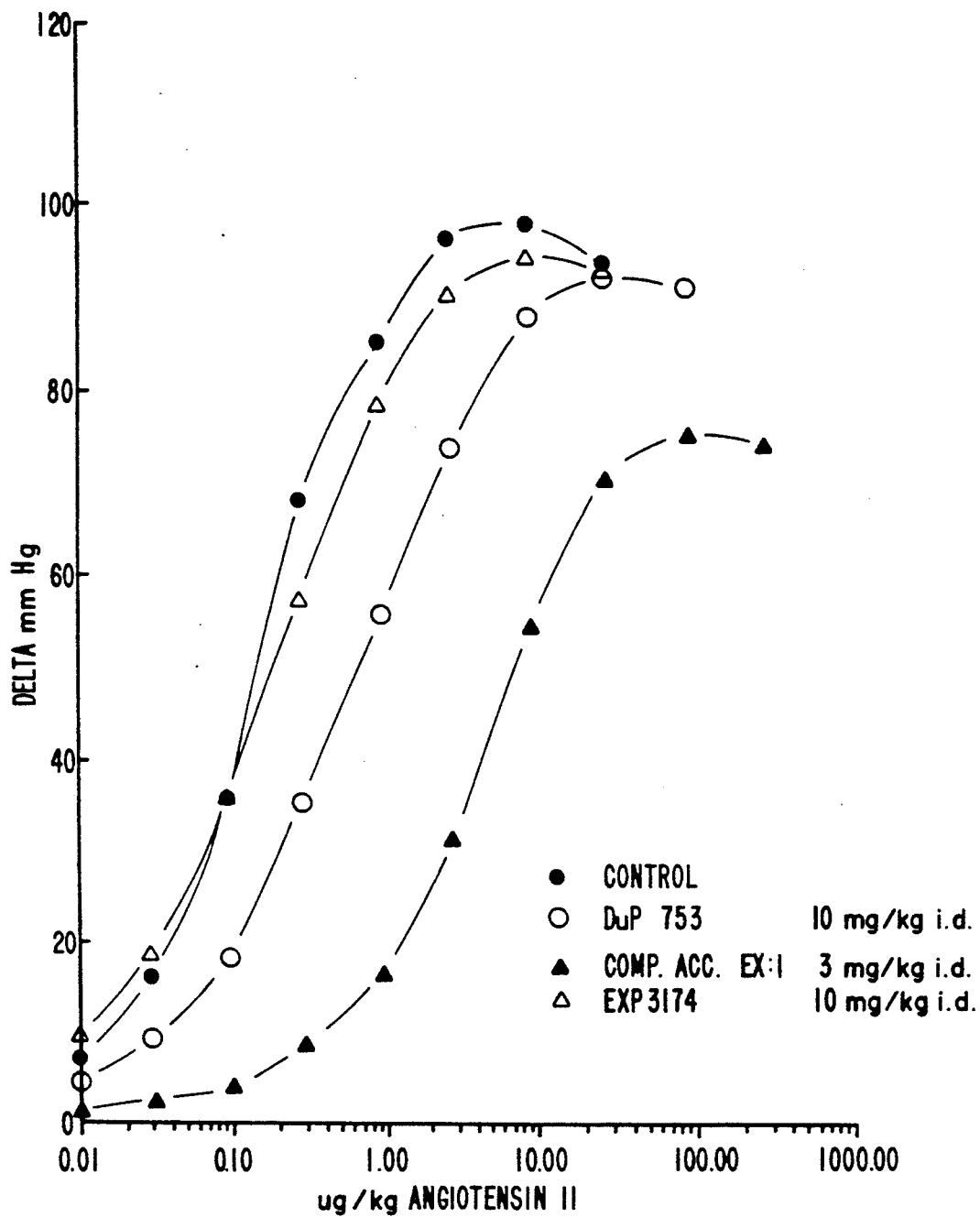
FIG. 4 depicts further the effect of known and prior art intraduodenally administered compounds on angiotensin II induced increases of diastolic blood pressure in pithed rats.

After intravenous administration, the compound according to Example 1 (0.3-10 mg/kg i.v.) was slightly more potent than DuP 753 (1-10 mg/kg i.v.) and about as potent as EXP 3174. After intraduodenal administration, the compound according to Example 1 proved to be by far the most potent substance. A sequence of intraduodenal potency of the compound according to Example 1>DuP 753>EXP 3174 results. (FIG. 4).

Figure 5:
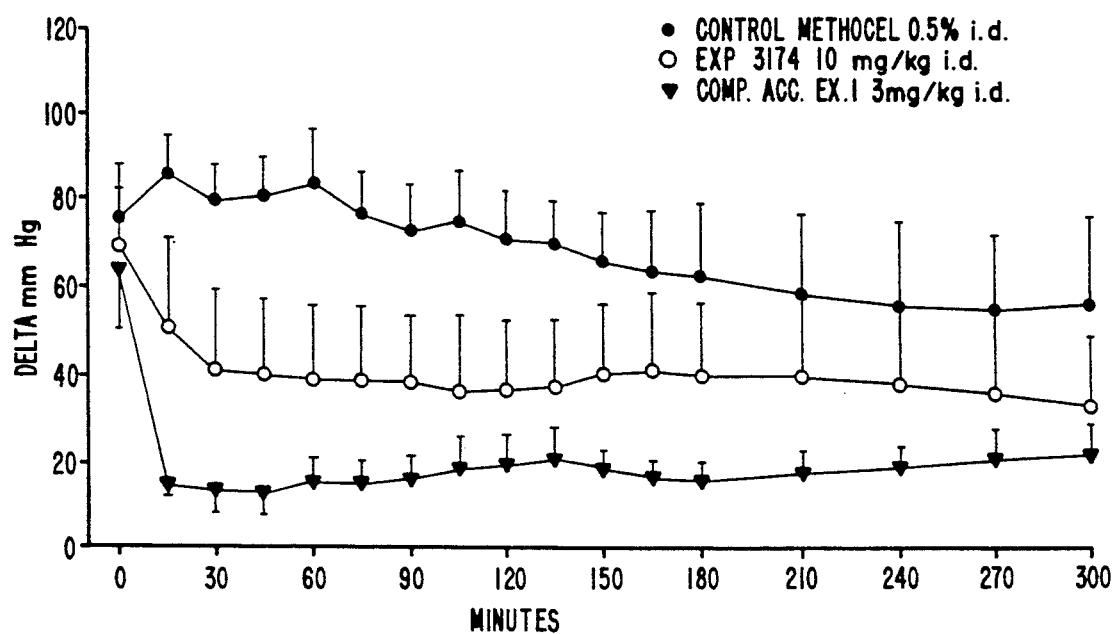
FIG. 5 depicts the effect of known and prior art intraduodenally administered compounds on angiotensin II induced increases of mean arterial blood pressure in anaesthetized, normotensive rats.
Figure 6A:
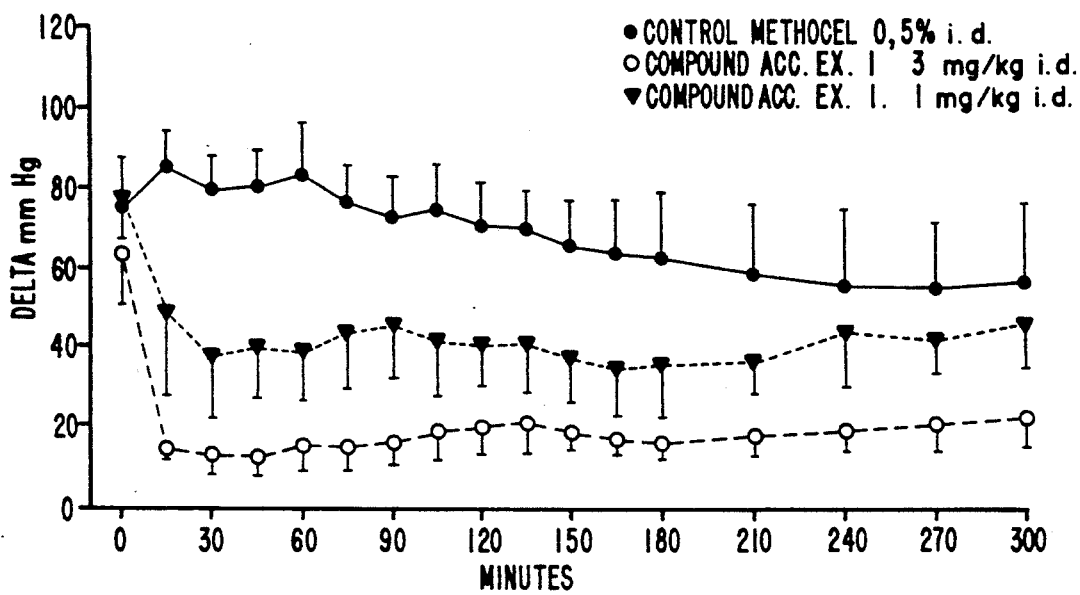
FIGS. 6a) and b) depict the effect of known and prior art intraduodenally administered compounds on antiotensin II induced increases in mean arterial blood pressure in normotensive rats.
Figure 6B:
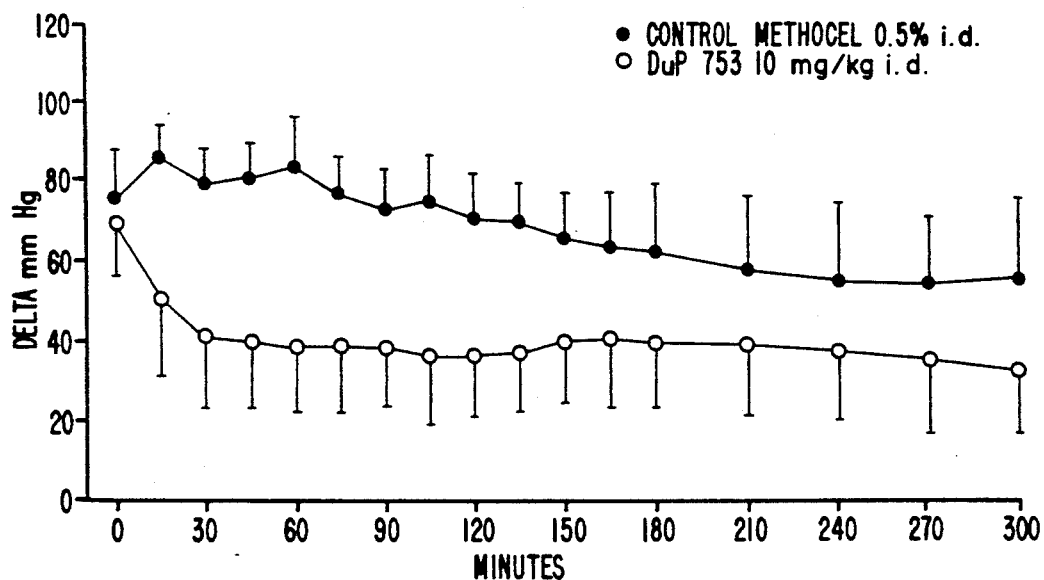

The duration of action of the substance was determined in anaesthetized, normotensive rats. Angiotensin II (1 μg.kg) was administered intravenously before substance administration and at 15 minute intervals after intraduodenal substance administration. Again, a sequence of potency of the compound according to Example 1>DuP 753 resulted. 3 mg/kg of the compound according to Example 1 were about twice as effective as 10 mg/kg of DuP 753 (FIG. 5). The compound according to Example 1 showed a particularly rapid, dose-dependent onset of action. The maximum angiotensin antagonistic action of the compound according to Example 1 was already achieved 15 minutes after intraduodenal administration (3 mg/kg), in contrast to 30–60 minutes after administration of DuP 753 (FIG. 6). The action of the substances remained constant over the total test period of 5 hours.

What we claim is:

1. An imidazole-5-carboxylic acid acylal of the formula:

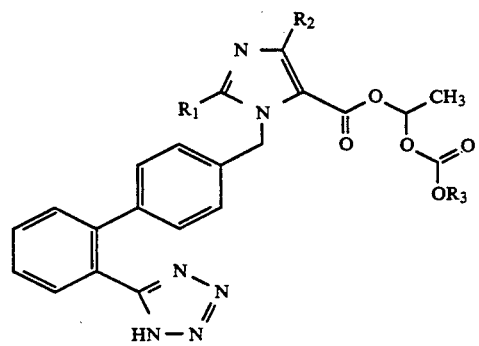

in which:

R$_1$ denotes a straight chain alkyl group having 1–6 carbon atoms or a straight chain alkenyl group having 2 to 6 carbon atoms, R$_2$ denotes hydrogen, chlorine, bromine or CF$_3$ and R$_3$ denotes C$_1$-C$_{10}$ alkyl; C$_3$-C$_7$ cycloalkyl or benzyl or their pharmaceutically acceptable salts.

2. The imidazole-5-carboxylic acid acylal defined in claim 1, in which R$_1$ denotes butyl.

3. The imidazole-5-carboxylic acid acylal according to claim 2 in which R$_2$ denotes chlorine.

4. 1-Ethoxycarbonyloxyethyl 2-butyl-4-chloro-1-((2'-(1H-tetrazol-5-yl)-biphenyl-4-yl)methyl-1H-imidazol-5-carboxylate.

5. 1-Ethoxycarbonyloxyethyl 2-butyl-4-chloro-1-((2'-)1H-tetrazol-5-yl)-biphenyl-4-yl)methyl-1H-imidazol-5-carboxylate, sodium salt.

6. A pharmaceutical composition for oral administration which contains 0.1-50 mg of a compound of the formula:

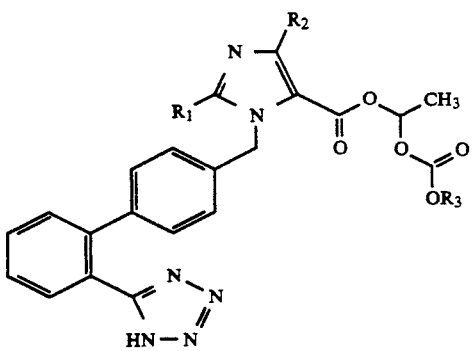

in which:
R₁ denotes a straight chain alkyl having 1–6 carbon atoms or a straight chain alkenyl group having 2 to 6 carbon atoms,
R₂ denotes hydrogen, chlorine, bromine or CF₃
and R₃ denotes C₁-C₁₀ alkyl; C₃-C₇ cycloalkyl or benzyl or a pharmaceutically acceptable salt thereof,
together with a pharmaceutically acceptable excipient or diluent.

7. A method of treating diseases which can be alleviated or cured by inhibiting angiotensin II which comprises administering to a patient in need of such treatment 0.1–30 mg/kg per day of a compound of the formula

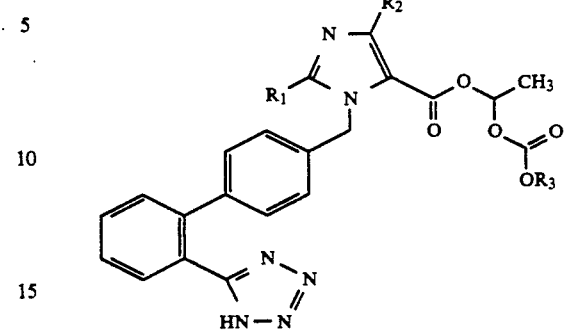

in which
R₁ denotes a straight chain alkyl having 1–6 carbon atoms or straight chain alkenyl group having 2 to 6 carbon atoms
R₂ denotes hydrogen, chlorine, bromine or CF₃
and R₃ denotes C₁-C₁₀ alkyl; C₃-C₇ cycloalkyl or benzyl or pharmaceutically acceptable salts thereof.

8. The method according to claim 7 wherein the disease is hypertension.

* * * * *